US009775925B2

(12) United States Patent
Juarez

(10) Patent No.: US 9,775,925 B2
(45) Date of Patent: *Oct. 3, 2017

(54) SCENT WARMERS AND RELATED METHODS

(71) Applicant: Scentsy, Inc., Meridian, ID (US)

(72) Inventor: Brandon Juarez, Eagle, ID (US)

(73) Assignee: Scentsy, Inc., Meridian, ID (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/686,689

(22) Filed: Apr. 14, 2015

(65) Prior Publication Data

US 2015/0231296 A1    Aug. 20, 2015

Related U.S. Application Data

(63) Continuation of application No. 14/532,509, filed on Nov. 4, 2014, now Pat. No. 9,345,800, which is a
(Continued)

(51) Int. Cl.
*H05B 1/00* (2006.01)
*A61L 9/03* (2006.01)
*H05B 3/00* (2006.01)

(52) U.S. Cl.
CPC .............. *A61L 9/03* (2013.01); *H05B 3/0071* (2013.01)

(58) Field of Classification Search
CPC ....... H05B 3/00; F21Y 2101/00; F21V 33/00; F27D 11/00; A61M 16/00; H01R 43/16; H01R 13/40
(Continued)

(56) References Cited

U.S. PATENT DOCUMENTS 5,651,942 A    7/1997    Christensen
5,903,710 A    5/1999    Wefler et al.
(Continued)

FOREIGN PATENT DOCUMENTS

CN    201187762 Y    1/2009
CN    201304124 Y    9/2009
(Continued)

OTHER PUBLICATIONS

International Preliminary Report on Patentability for International Application No. PCT/US2012/041309, dated Dec. 17, 2013, 6 pages.
(Continued)

*Primary Examiner* — Phuong Nguyen
(74) *Attorney, Agent, or Firm* — TraskBritt

(57) ABSTRACT

A scent warmer may include an at least substantially hollow member having at least one inner surface defining an internal cavity therein, a receptacle disposed at a first longitudinal end of the at least substantially hollow member for holding scented material therein, and a support structure configured to support at least one lighting module within the internal cavity of the at least substantially hollow member. The support structure may be a separate member from the at least substantially hollow member. The at least substantially hollow member may be configured to conceal at least substantially all of the support structure when the at least substantially hollow member is placed over the support structure on a flat surface.

19 Claims, 12 Drawing Sheets

Related U.S. Application Data continuation of application No. 13/160,790, filed on Jun. 15, 2011, now Pat. No. 8,878,102.

(58) Field of Classification Search
USPC ........ 363/641, 650, 657–659, 642–644, 253, 363/264, 580, 263, 228, 231; 219/209, 219/438; 431/219, 289, 292, 298, 294
See application file for complete search history.

(56) References Cited

U.S. PATENT DOCUMENTS

| | | | |
|---|---|---|---|
| 5,945,094 A | 8/1999 | Martin et al. | |
| 6,085,026 A | 7/2000 | Hammons et al. | |
| 6,106,786 A * | 8/2000 | Akahoshi | A61L 9/122 222/187 |
| 6,354,710 B1 | 3/2002 | Nacouzi | |
| 6,398,544 B2 * | 6/2002 | Wright | F23D 3/16 431/289 |
| 6,478,440 B1 | 11/2002 | Jaworski et al. | |
| 6,527,418 B1 * | 3/2003 | Scherba | 362/294 |
| 6,627,857 B1 | 9/2003 | Tanner et al. | |
| 6,779,905 B1 | 8/2004 | Mazursky et al. | |
| 6,805,300 B2 | 10/2004 | Munroe et al. | |
| 6,917,754 B2 | 7/2005 | Pedrotti et al. | |
| 6,966,665 B2 | 11/2005 | Limburg et al. | |
| 7,046,919 B2 | 5/2006 | Shimizu et al. | |
| 7,121,686 B1 | 10/2006 | Chu | |
| 7,133,605 B2 * | 11/2006 | Niemeyer | 392/390 |
| 7,186,016 B2 | 3/2007 | Jao | |
| 7,246,919 B2 | 7/2007 | Porchia et al. | |
| 7,277,626 B2 | 10/2007 | Pesu et al. | |
| 7,318,659 B2 | 1/2008 | Demarest et al. | |
| 7,350,720 B2 | 4/2008 | Jaworski et al. | |
| 7,419,281 B2 | 9/2008 | Porchia et al. | |
| 7,455,444 B2 | 11/2008 | Chien | |
| 7,476,002 B2 | 1/2009 | Wolf et al. | |
| 7,481,571 B2 | 1/2009 | Bistritzky et al. | |
| 7,484,860 B2 | 2/2009 | Demarest et al. | |
| 7,503,668 B2 | 3/2009 | Porchia et al. | |
| 7,503,675 B2 | 3/2009 | Demarest et al. | |
| 7,543,957 B1 | 6/2009 | Balazs et al. | |
| 7,572,412 B2 | 8/2009 | Yang | |
| 7,611,253 B2 | 11/2009 | Chien | |
| 7,618,151 B2 | 11/2009 | Abbondanzio et al. | |
| 7,641,364 B2 | 1/2010 | Abbondanzio et al. | |
| 7,687,744 B2 | 3/2010 | Walter et al. | |
| 7,699,603 B2 | 4/2010 | Furner et al. | |
| 7,824,627 B2 | 11/2010 | Michaels et al. | |
| 7,839,068 B2 | 11/2010 | Hayashi et al. | |
| 7,932,482 B2 | 4/2011 | Norwood et al. | |
| 8,772,675 B2 | 7/2014 | Juarez | |
| 2005/0016985 A1 * | 1/2005 | Haas | A61L 9/03 219/438 |
| 2005/0184045 A1 | 8/2005 | Shimizu et al. | |
| 2005/0195600 A1 | 9/2005 | Porchia et al. | |
| 2006/0152946 A1 | 7/2006 | Chien | |
| 2007/0086199 A1 * | 4/2007 | Demarest et al. | 362/441 |
| 2008/0279731 A1 | 11/2008 | Goreham et al. | |
| 2009/0025567 A1 * | 1/2009 | Greenberg et al. | 99/337 |
| 2009/0073694 A1 | 3/2009 | Scannell, Jr. | |
| 2009/0196587 A1 | 8/2009 | Cheung | |
| 2009/0289047 A1 | 11/2009 | Hisao | |
| 2010/0096376 A1 | 4/2010 | Hsiao | |
| 2010/0260646 A1 | 10/2010 | Jorgensen | |
| 2010/0270943 A1 * | 10/2010 | Cook | 315/291 |
| 2010/0290254 A1 | 11/2010 | Howard et al. | |
| 2011/0110092 A1 * | 5/2011 | Hsiao | 362/253 |
| 2011/0110118 A1 | 5/2011 | Hsiao | |
| 2011/0110824 A1 | 5/2011 | Hsiao | |
| 2011/0267821 A1 | 11/2011 | Van De Ven et al. | |
| 2012/0024837 A1 | 2/2012 | Thompson | |

FOREIGN PATENT DOCUMENTS

| | | | |
|---|---|---|---|
| CN | 201510547 U | 6/2010 | |
| CN | 201651990 U | 11/2010 | |
| CN | 201696973 U | 1/2011 | |
| DE | 202009005303 U1 | 8/2009 | |
| DE | 202009014766 U1 | 3/2010 | |
| EP | 884078 B1 | 3/2004 | |
| JP | 2001327588 A | 11/2001 | |
| JP | 3146210 U | 10/2008 | |
| JP | 3146211 U | 10/2008 | |
| TW | 200909009 A | 3/2009 | |
| TW | M356511 U | 5/2009 | |
| TW | M356511 U * | 5/2009 | A61L 9/03 |
| WO | 2005074999 A1 | 8/2005 | |
| WO | 2009027668 A1 | 3/2009 | |
| WO | 2009027670 A1 | 3/2009 | |
| WO | 2010062529 A2 | 6/2010 | |
| WO | 2010135789 A1 | 12/2010 | |

OTHER PUBLICATIONS

International Written Opinion for International Application No. PCT/US2012/041309, mailed Mar. 4, 2013, 5 pages.
International Search Report for International Application No. PCT/US2012/041309, mailed Mar. 4, 2013, 4 pages.
Letter Dated Nov. 18, 2013 from Lynn G. Foster to J. Jeffrey Gunn and Stephen E. Pulley with Enclosures; Candle Warmer "the original alternative to lighting a candle" Product Guide 2005, www.candlewarmers.com, 6 pages; color photograph.
Search Report from Taiwan Patent Application No. 101121447, dated May 19, 2016, 1 page.

* cited by examiner

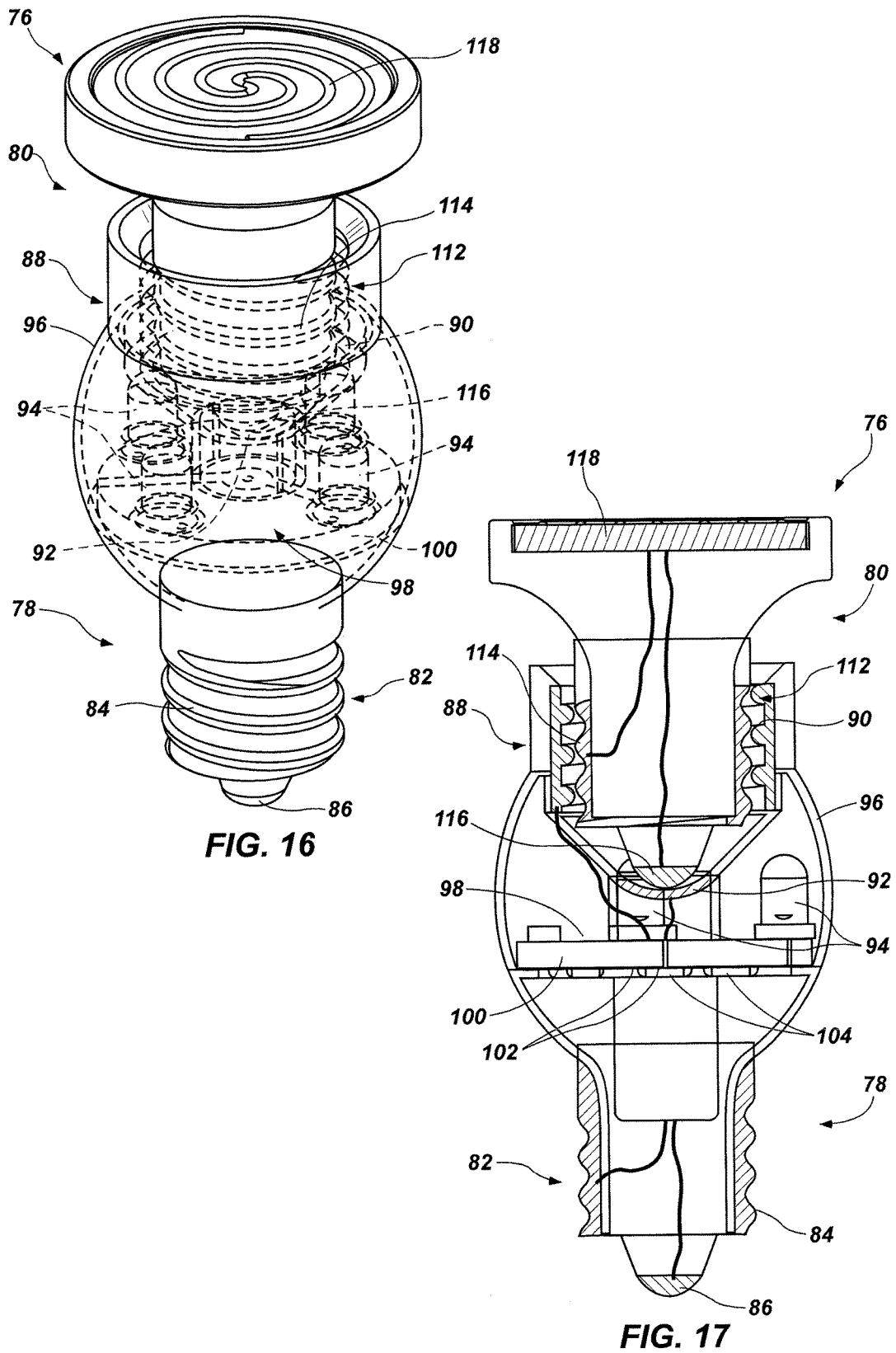

SCENT WARMERS AND RELATED METHODS

CROSS-REFERENCE TO RELATED APPLICATIONS

This application is a continuation of U.S. patent application Ser. No. 14/532,509, filed Nov. 4, 2014, now U.S. Pat. No. 9,345,800, issued May 24, 2016, which is a continuation of U.S. patent application Ser. No. 13/160,790, filed Jun. 15, 2011, now U.S. Pat. No. 8,878,102, issued Nov. 4, 2014, the disclosure of each of which is hereby incorporated herein in its entirety by this reference. The subject matter of this application is also related to U.S. patent application Ser. No. 13/092,697, filed Apr. 22, 2011, now U.S. Pat. No. 9,211,355, issued Dec. 15, 2015, which claims priority to U.S. Provisional Patent Application Ser. No. 61/368,181, filed Jul. 27, 2010. In addition, the subject matter of this application is also related to U.S. patent application Ser. No. 14/801,577, filed Jul. 16, 2015, pending, which is a continuation of U.S. patent application Ser. No. 14/301,149, filed Jun. 10, 2014, now U.S. Pat. No. 9,125,956, issued Sep. 8, 2015, which is a continuation of U.S. patent application Ser. No. 13/160,842, filed Jun. 15, 2011, now U.S. Pat. No. 8,772,675, issued Jul. 8, 2014.

FIELD

Embodiments of the disclosure relate generally to scent warmers. More particularly, embodiments of the disclosure relate to base structures for scent warmers that enable a user to easily connect, exchange, and replace power cords and to switch the scent warmers on and off. In addition, embodiments of the disclosure relate to base structures with increased rigidity and strength that include electrical connections having increased rigidity and strength.

BACKGROUND

Candles made from scented wax have been used to create an aroma in a surrounding area. Typically, candles include a wick that may be lit by a flame. The burning wick melts the wax near the wick and pulls the liquid wax, along with the scents included in the wax, up into the wick by capillary action or absorption. The flame burns the scented wax, and an aroma is released into the area surrounding the candle. The flame of the traditional candle also produces light, which is often regarded as desirable for creating a pleasing ambience or for providing energy efficient light, for example. While light and an aroma are produced by candles, traditional candles produce some risks and hazards, including a risk of burns, fires, and smoke.

Scent warmers have been used, as an alternative to candles, to heat scented wax or scented oil. Scent warmers are often referred to as flameless candles or wickless candles. Some scent warmers release the aroma from the scented wax or oil without the use of a flame. For example, scent warmers may include a base that houses an incandescent light bulb acting as a heat source. The incandescent light bulb is positioned inside the base under a plate holding the scented wax or oil. The incandescent light bulb heats the bottom of the plate primarily through radiation and convection. The plate, in turn, heats the wax or oil, thus releasing the scent into the surrounding area by increasing the rate of evaporation or dissipation of the scented material. Such scent warmers are generally safer than traditional candles because of the absence of a flame. However, incandescent light bulbs are generally seen as inefficient and may include their own disadvantages. For example, incandescent bulbs may need frequent replacement, adding to the cost of operating the scent warmer.

Other scent warmers use a resistive heating element, rather than an incandescent light bulb, to heat scented wax or oil. Such scent warmers may include a plate for holding scented wax or oil with a resistive heating element attached to the bottom of the plate. The heating element heats the plate primarily by conduction, and the plate transfers the heat to the scented wax or oil, thereby releasing an aroma into the surrounding area. However, such scent warmers do not produce light.

Still other scent warmers, such as those disclosed in U.S. patent application Ser. No. 13/092,697, which was filed Apr. 22, 2011 and is entitled "Scent Warmers Having Non-Incandescent Heating and Light-Emitting Devices and Related Methods," may produce light by including light sources, such as light-emitting diodes (LEDs) or compact fluorescent lamps (CFLs) within a base, which may include holes, translucent portions, or transparent portions that allow light to pass from the base interior to the base exterior.

The constituent parts of the any of the foregoing scent warmers, however, may not be easily accessible, which may increase the difficulty or complexity of replacing the constituent parts of the scent warmer when those constituent parts are damaged, broken, or have simply exceeded their useful life. In addition, the power plugs typically connected to any of the foregoing scent warmers may be fixed to the scent warmer, requiring different scent warmers to be made for use in different geographical areas, which may employ different electrical socket configurations and different electrical power standards in terms of voltage, current, and frequency.

BRIEF DESCRIPTION OF THE DRAWINGS

While the specification concludes with claims particularly pointing out and distinctly claiming that which is regarded as the present invention, various features and advantages of embodiments of the disclosure may be more readily ascertained from the following description of embodiments of the disclosure when read in conjunction with the accompanying drawings, in which:

FIG. 16 depicts a perspective view an assembly of the lighting module of FIGS. 10 and 11 with the heating module of FIGS. 14 and 15; and FIG. 17 illustrates a cross-sectional view of the assembly of FIG. 16.

DETAILED DESCRIPTION

The illustrations presented herein are not meant to be actual views of any particular scent warmer, base structure for use with a scent warmer, or components or portions thereof, but are merely idealized representations that are employed to describe certain disclosed embodiments. Thus, the drawings are not necessarily to scale and relative dimensions may have been exaggerated for the sake of clarity or simplicity. Additionally, elements common between figures may retain the same or similar numerical designation.

Embodiments of the disclosure relate generally to scent warmers. More particularly, embodiments of the disclosure relate to base structures for scent warmers that enable a user to easily connect, exchange, and replace power cords and to switch the scent warmers on and off. In addition, embodiments of the disclosure relate to base structures with increased rigidity and strength that include electrical connections having increased rigidity and strength.

As used herein, any directional term (e.g., upper, lower, side, top, bottom, etc.) refers to a direction relative to the device when the device is used during normal operation. By way of non-limiting example, an upper portion of a scent warmer is the upper portion while the scent warmer is in an orientation for use, and used to warm scented material.

As used herein, the term "module" means and includes any independently operable unit that may be a part of an overall structure of an assembly. For example, a module may include a unit for providing light, a unit for providing heat, or a unit for providing both light and heat in a scent warmer assembly.

As used herein, the term "translucent" means and includes any material that exhibits less than 100% opacity. In other words, a translucent material permits at least some light to pass therethrough. For example, a translucent material may transmit and diffuse light so that objects cannot be seen clearly therethrough or may be completely transparent to visible light (i transmitting light without appreciable scattering) so that objects can be seen clearly therethrough.

Figure 1:
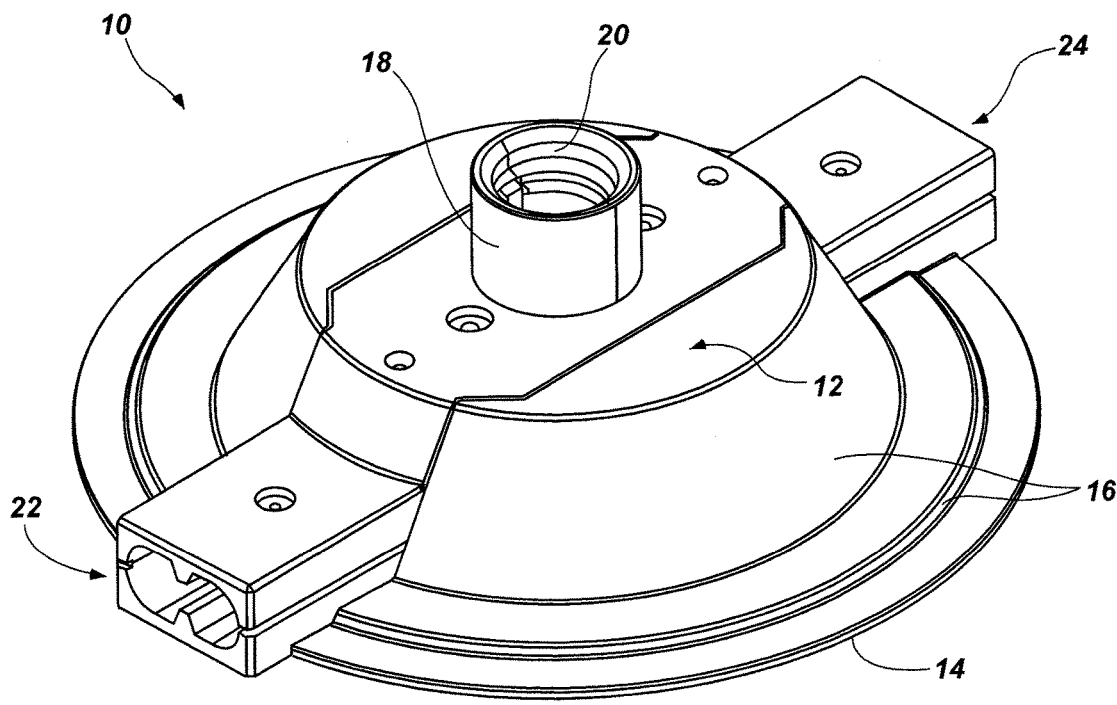
FIG. 1 is a perspective view of a base structure that may be used with a scent warmer.

Referring to FIG. 1, a perspective view of a base structure 10 that may be used with a scent warmer is shown. The base structure 10 comprises a support structure 12 on which an at least substantially hollow member defining a cavity may be received. By way of example, the support structure 12 may comprise an at least substantially planar lower surface 14, which may rest on another surface, such as, for example, a table or a counter. The support structure 12 may extend upwardly from the lower surface 14, and may at least substantially define an outer periphery of the base structure 10. The outer periphery of the base structure 10 at least partially defined by the support structure 12 may comprise, for example, a circle, an oval, a polygon, an irregular shape, or other geometric shapes. The support structure 12 may comprise, for example, a polymer, a ceramic, a metal, or another material suitable for use with a scent warmer. The support structure 12 may comprise a single integral part or may comprise a plurality of parts assembled to form the support structure 12.

The support structure 12 may include one or more retaining portions 16, over which an at least substantially hollow member defining an internal cavity of a scent warmer may be placed. For example, the retaining portions 16 may comprise substantially frustoconical protrusions over which cooperating recesses or holes in the at least substantially hollow member defining a cavity may be placed. Thus, the retaining portions 16 may be configured to receive another structure, to align the other structure over the base structure 10, and to resist displacement of the other structure relative to the base structure 10, for example, due to jostling, bumps, or due to placement on an uneven or inclined surface. The support structure 12 may comprise a series of retaining portions 16, for example, in a stepped configuration in some embodiments. In other embodiments, the support structure 12 may comprise a single retaining portion.

The base structure 10 may also include an electrical connector 18 extending upwardly from the support structure 12. The electrical connector 18 may comprise a male or a female electrical connector. By way of example, the electrical connector 18 may comprise a threaded electrical connector, a terminal block, a binding post, a crimp-on connector, a plug-and-socket connector, a blade connector, a ring and spade terminal, a bayonet-type electrical connector, a keyed-type electrical connector, a surface contact, or other types of electrical connectors 18 known in the art. As a specific, non-limiting example, the electrical connector 18 may comprise a female Edison screw fitting configured to threadedly engage and electrically communicate with an electrical connector comprising a male Edison screw fitting. Generally speaking, such an electrical connector 18 may comprise at least one helically extending recess 20 configured to engage and electrically communicate with at least one helically extending protrusion of a male Edison screw fitting and at least one lower contact (not shown) configured to abut and electrically communicate with a lower contact of the male Edison screw fitting.

Standards for Edison screw fittings may be obtained, for example, from the American National Standards Institute (ANSI). Edison screw fittings may specifically conform to ANSI Standard C81.61-2009, which sets forth specifications for bases or caps for electric lamps. Generally, Edison screw fittings comprise a right-hand threading that forms one of the contacts for a circuit and a bottom center portion that forms the other contact to close the circuit. By way of non-limiting example, the electrical connector 18 may comprise a standard E5, E5.5, E10, E11, E12, E14, E17, E26, E27, E39, or E40 Edison screw fitting, where the numbers following "E" may correspond to the diameter of the Edison screw fitting in millimeters. As a specific, non-limiting example, the electrical connector 18 may comprise a standard E11 Edison screw fitting, which may correspond to a standard candelabra size Edison screw fitting as used in Europe. As another specific, non-limiting example, the electrical connector 18 may comprise a standard E27, also known in the art as a standard "ES," Edison screw fitting, which may correspond to a medium, or standard size, light bulb Edison screw fitting as used in Europe.

The base structure 10 may further include a power cord connector 22 physically connected to the support structure 12. The power cord connector 22 may be located at the periphery of the base structure 10. The power cord connector 22 may extend beyond the outer limits of the support structure 12 in some embodiments. In other embodiments, the power cord connector 22 may be flush with an outermost surface of the support structure 12. In still other embodiments, an end of the power cord connector 22 may terminate at a location that does not reach the radially outermost surface of the support structure 12. The power cord connector 22 may be configured to physically secure and electrically communicate with a power cord. Thus, the power cord connector 22 may enable the base structure 10 to connect with power cords, for example, to replace a damaged or otherwise inoperable power cord or to attach a power cord having a different power plug, such as, for example, an AC power plug configured for use with an AC power socket of a required configuration for use in a particular geographic area. The power cord connector 22 may be in constant or selective electrical communication with the electrical connector 18. Thus, an external electrical power source may provide electrical power to the electrical connector 18 through the power cord connector 22.

The base structure 10 may optionally include a switch 24 for selectively communicating the electrical connector 18 with a power source connected through the power cord connector 22. The switch 24 may comprise a conventional, manually operated switch 24. The switch 24 may be physically connected to the support structure 12 and interposed in the electrical pathway between the electrical connector 18 and the power cord connector 22. Thus, the switch 24 may enable a user to close an otherwise open electrical pathway from an input contact of the power cord connector 22, through the switch, to the electrical connector 18, and to an output contact of the power cord connector 22. The switch 24 may be located at the periphery of the base structure 10. The switch 24 may extend beyond the outer limits of the support structure 12 in some embodiments. In other embodiments, the switch 24 may be flush with an outermost surface of the support structure 12. In still other embodiments, an end of the switch 24 may terminate at a location that does not reach the radially outermost surface of the support structure 12.

The switch 24 and the power cord connector 22 may be located anywhere around the periphery of the base structure 10, and may be located in any suitable relative positions to one another. For example, the switch 24 may be located on a side of the base structure 10 opposing a side on which the power cord connector 22 is located. As another example, the switch 24 may be located on the same side of the base structure 10 as the power cord connector 22 and may be immediately adjacent the power cord connector 22. As yet another example, the switch 24 may be located on the same side of the base structure 10 as the power cord connector 22 and may be aligned with and positioned over or under the power cord connector 22. Stated another way, the switch 24 may extend in a direction parallel to the direction in which the power cord connector 22 extends and may be located directly above or directly below the power cord connector 22 in some embodiments.

Figure 2:
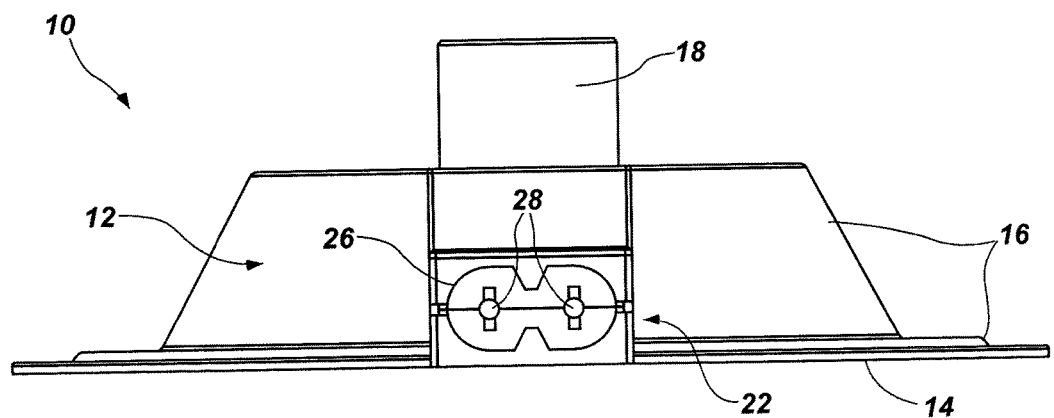
FIG. 2 depicts a side view of the base structure of FIG. 1.

Referring to FIG. 2, a side view of the base structure 10 of FIG. 1 is shown. The power cord connector 22 may be configured to physically and electrically connect with a power cord. The power cord connector 22 may be configured to physically secure a power cord using an interference fit or a snap fit physical connection. By way of example, the power cord connector 22 may comprise a recess 26 into which a cooperating portion of a power cord may be inserted. The recess 26 may be of a size and shape that, when the cooperating portion of a power cord is inserted into the recess 26, frictional forces between abutting surfaces of the power cord connector 22 and the power cord physically retain the power cord. The power cord connector 22 may be configured to electrically communicate with a power cord using electrically conductive materials in contact with one another. For example, the power cord connector 22 may comprise electrically conductive prongs 28 located within the recess 26 that may be contacted by an electrically conductive portion of a power cord.

The power cord connector 22 may comprise a standard electrical-coupler-and-inlet configuration in some embodiments. Standards for coupler-and-inlet power cord connectors 22 may be obtained, for example, from the International Electrotechnical Commission (IEC). Coupler-and-inlet power cord connectors 22 may specifically conform to IEC Standard 60320-1, which sets forth specifications for two-pole couplers for the connection of power supply cords to electrical appliances. Generally, coupler-and-inlet power cord connectors 22 comprise an inlet, typically located on the appliance to which electrical power is supplied, that interfaces with a complementary coupler, typically located on the power cord. As a specific, non-limiting example, the power cord connector 22 may comprise a standard C8 inlet.

Figure 3:
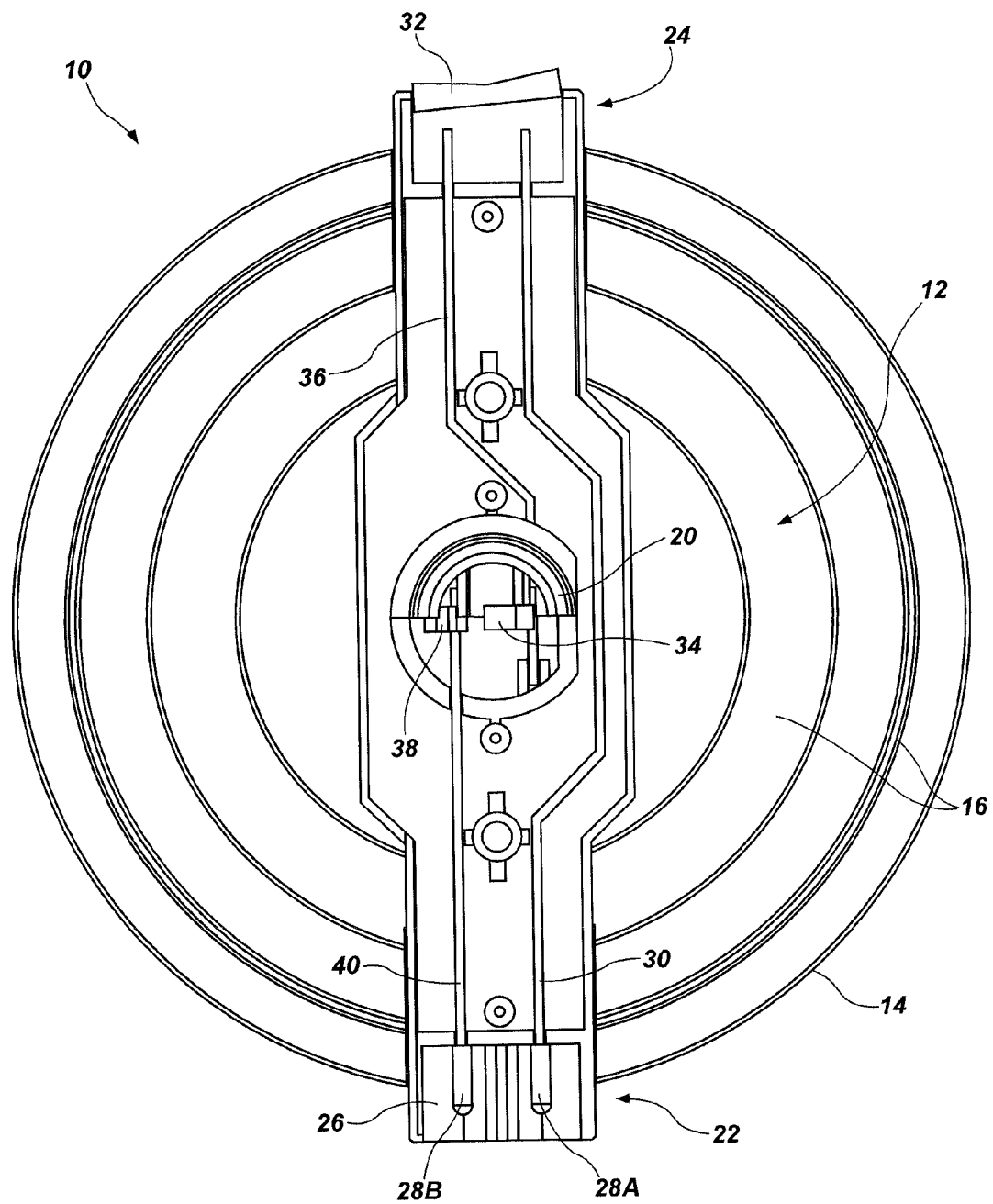
FIG. 3 illustrates a partial cutaway plan view of the base structure of FIG. 1.
Figure 4:
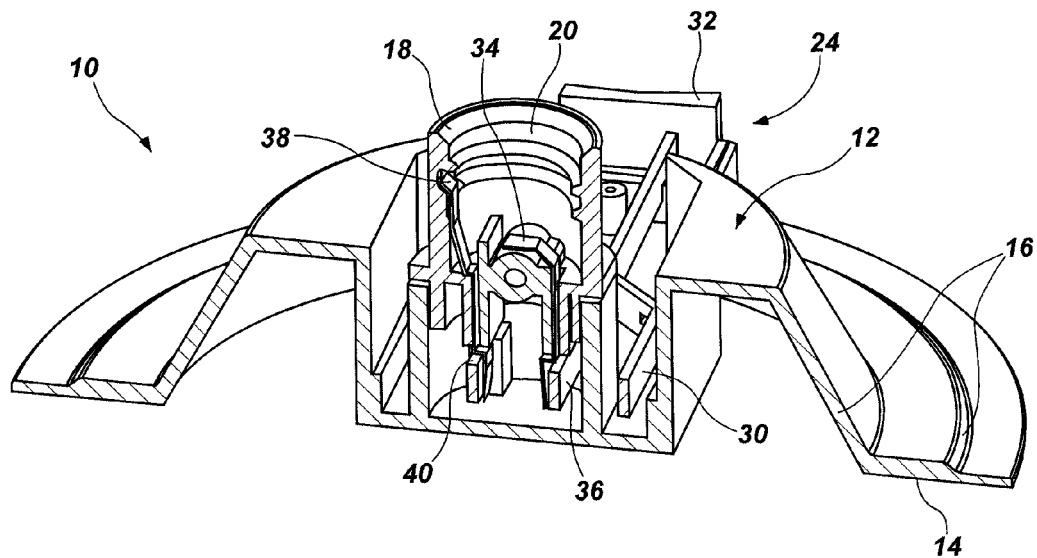
FIGS. 4 and 5 are partial cutaway perspective views of the base structure of FIG. 1.
Figure 5:
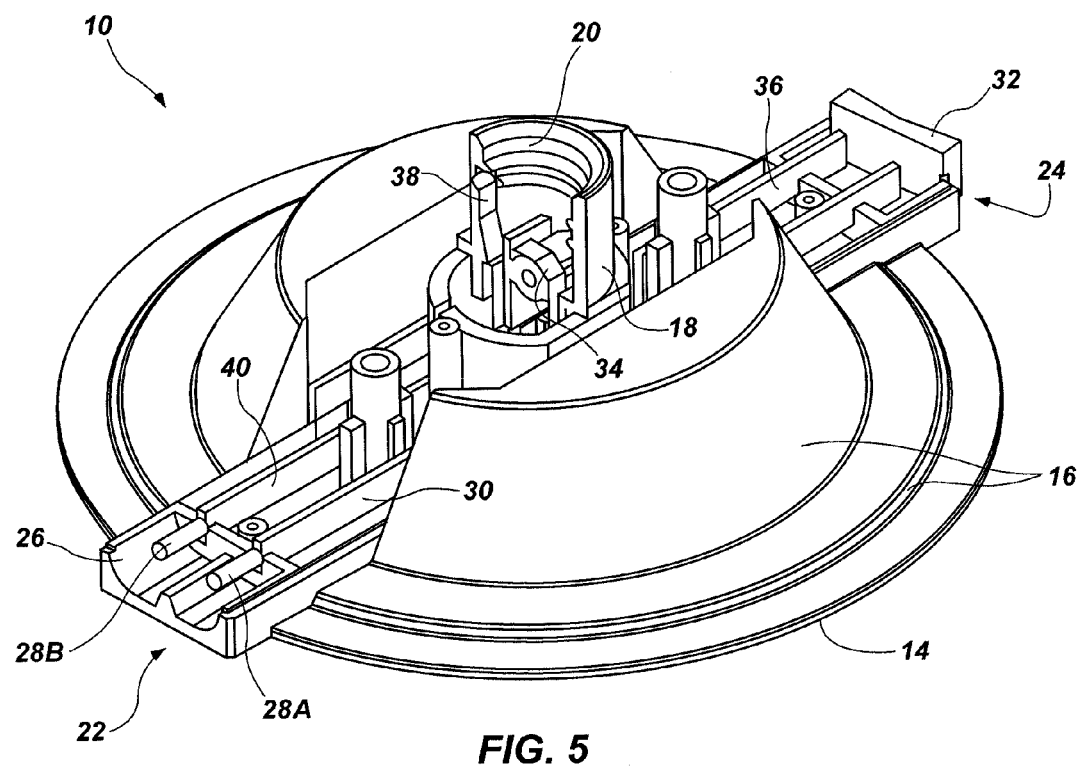

Referring to FIGS. 3 through 5, a partial cutaway plan view and two partial cutaway perspective views of the base structure 10 of FIG. 1 are shown, respectively. By way of example, the electrical pathway of the base structure 10 may comprise a first prong 28A of the power cord connector 22, which may be directly electrically connected to the switch 24. The direct electrical connection may be made using, for example, a first strip 30 of electrically conductive material. The switch 24 may be manipulated by a user to selectively open and close the electrical pathway by displacing a switching member 32 to "off" and "on" positions. Other components of the switch 24 are not shown for the sake of simplicity, but the switch 24 may comprise any type of manually operated electrical switch known in the art.

The switch 24 may be directly electrically connected to the electrical connector 18. The direct electrical connection may be made using, for example, a second strip 34 of electrically conductive material, such as copper metal, extending upwardly toward the electrical connector 18 electrically connected to a third strip 36 extending between the switch 24 and the second strip 34. The second strip 34 of electrically conductive material may comprise one of the contacts of the electrical connector 18, such as, for example, the lower contact as described previously. In embodiments where an optional switch 24 is not interposed in the electrical pathway between the power cord connector 22 and the electrical connector 18, the first prong 28A of the power cord connector 22 may be directly electrically connected to the electrical connector 18.

The electrical connector 18 may be directly electrically connected to a second prong 28B of the power cord connector 22. The direct electrical connection may be made using, for example, a fourth strip 38 of electrically conductive material extending downwardly from the electrical connector 18 electrically connected to a fifth strip 40 of electrically conductive material extending between a second prong 28B of the power cord connector 22 and the fourth strip 38. The fourth strip 38 of electrically conductive material may comprise another of the contacts of the electrical connector 18, such as, for example, a contact within the helically extending recess 20 as described previously. Thus, a closed electrical pathway may be formed when the switch 24 is in a closed, or "on," position and a lighting, heating, or heating and lighting module is electrically connected to the electrical connector 18. Each of the strips 30, 34, 36, 38, and 40 of electrically conductive material may comprise a rigid metal member of rectangular cross-section, for example, as best shown in FIG. 4. In alternative embodiments, wired connections may be used in place of the various strips 30, 34, 36, 38, and 40 of electrically conductive material. Using strips 30, 34, 36, 38, and 40 of electrically conductive material, such as a metal may, however, increase reliability of the base structure 10 by reducing bending, warping, and breakage of the electrical connections due to the increased rigidity and strength of the strips 30, 34, 36, 38, and 40 in comparison to that of conventional wires.

As also best illustrated in FIG. 4, the retaining portions 16 may increase the rigidity of the support structure 12. For example, the substantially frustoconical protrusions of the retaining portions 16 may increase the rigidity and strength of the support structure 12 when compared to a support structure 12 that is substantially planar or disc-shaped without any protrusions. Thus, the base structure 10 may comprise a relatively rigid support structure 12 having rigid electrical connections therein, which may increase the strength and reliability of the base structure 10.

Figure 6:
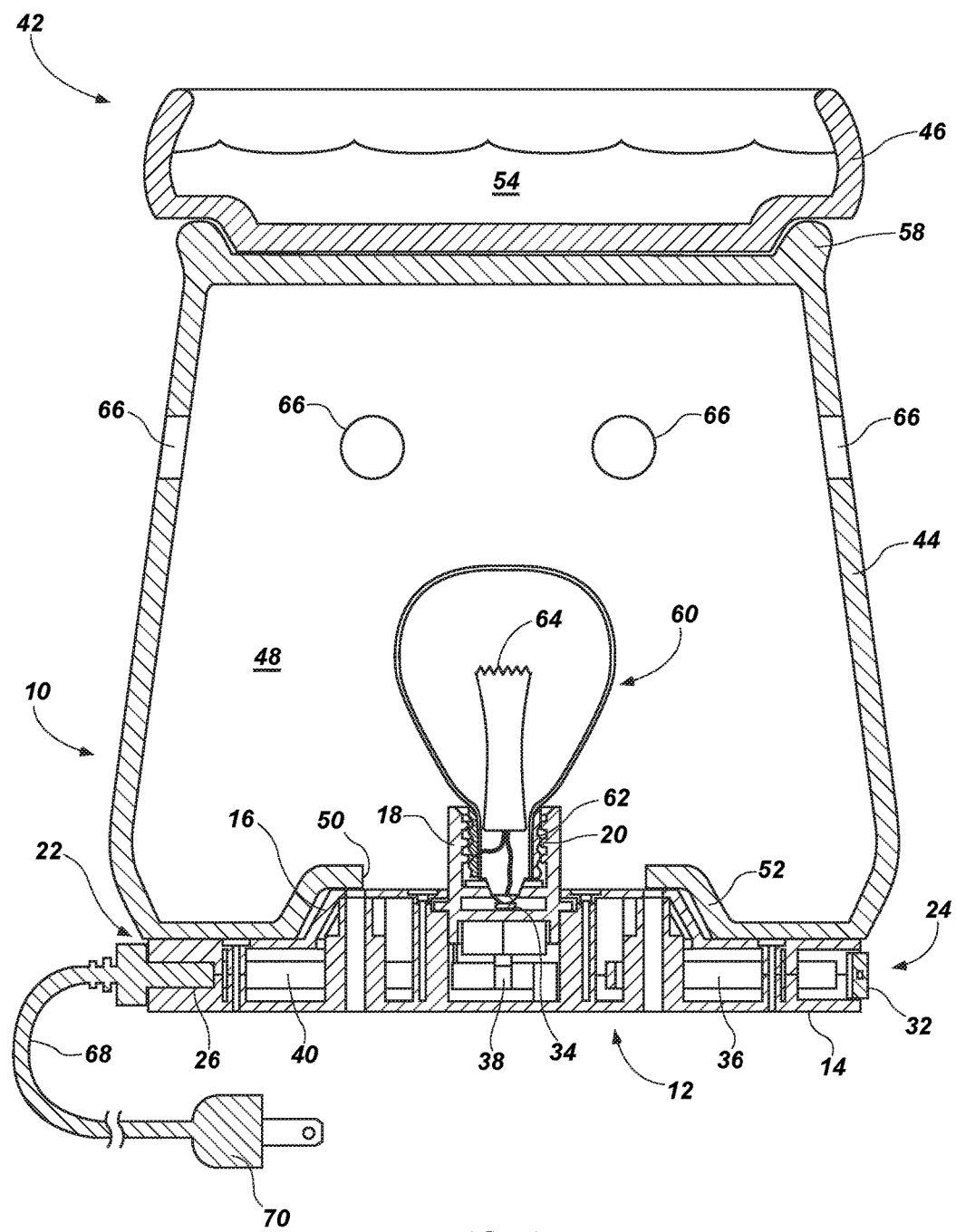
FIG. 6 depicts a cross-sectional view of a scent warmer.

Referring to FIG. 6, a cross-sectional view of a scent warmer 42 is shown. The scent warmer 42 may comprise a base structure 10. In addition to the support structure 12, the electrical connector 18, the power cord connector 22, and the optional switch 24 described previously, the base structure 10 may include an at least substantially hollow member 44 and a receptacle 46. The at least substantially hollow member 44 may define a cavity 48 configured to receive at least one of a lighting, heating, and lighting and heating module at least partially therein. At least one of a lighting, heating, and lighting and heating module may be received at least partially into the cavity 48 through a lower opening 50 in the at least substantially hollow member 44. The at least substantially hollow member 44 may be disposed on and supported by the support structure 12. For example, the at least substantially hollow member 44 may comprise a complementary retaining portion 52, such as, for example, a substantially frustoconical taper, which may align with and abut against the retaining portion 16 of the support structure 12. The at least substantially hollow member 44 may be formed from, for example, a ceramic, a polymer, a metal, or other materials suitable for use with scent warmers.

The receptacle 46 may be disposed over the at least substantially hollow member 44. The receptacle 46 may comprise, for example, an upwardly facing cup-shaped member in which a scented material 54 may be disposed. The receptacle 46 may be removable from the at least substantially hollow member 44. For example, the at least substantially hollow member 44 may include an upper surface 56 on which the receptacle 46 may be disposed during use and an upwardly projecting peripheral ridge 58, which may also be characterized as a lip that may be used to retain and align the receptacle 46 on the upper surface 56. The receptacle 46 may comprise the same material as the at least substantially hollow member 44 in some embodiments. In other embodiments, the receptacle 46 may comprise a different ceramic, polymer, metal, or other suitable material for use with scent warmers from the at least substantially hollow member 44. By making the receptacle 46 a separate structure from the at least substantially hollow member 44, the receptacle 46 may be easily removed to exchange for another receptacle 46 (e.g., to change the appearance of the scent warmer 42 or to replace a lost, damaged, or broken receptacle 46) or to clean the receptacle 46, for example.

The scent warmer 42 may include at least one of a lighting, heating, and lighting and heating module. For example, the lighting, heating, or lighting and heating module may comprise an incandescent lamp 60. The incandescent lamp 60 may be at least partially disposed within the cavity 48 defined by the at least substantially hollow member 44. The incandescent lamp 60 may comprise an electrical connector 62, which may be engaged and in electrical communication with the electrical connector 18 of the base structure 10. For example, the electrical connector 62 of the incandescent lamp 60 may comprise an Edison screw fitting, which may threadedly engage the helically extending recess 20 of the electrical connector 18 of the base structure 10 and which may electrically connect with the second and fourth strips 34 and 38 of the base structure 10. Thus, the electrical connector 18 of the base structure 10 may extend from the support structure 12 toward the cavity 48 defined by the at least substantially hollow member 44. The incandescent lamp 60 may include an electrical light and heat source located above and in electrical communication with the electrical connector 62 of the incandescent lamp 60. For example, the incandescent lamp 60 may include a filament 64 configured to emit both light and heat as electric current flows through the filament 64. The filament 64 may comprise, for example, a coiled tungsten wire. The heat emitted by the incandescent lamp 60 may cause scented material 54 supported by the receptacle 46 to release a scent into the surrounding environment.

The at least substantially hollow member 44 may be configured to permit light emitted by the incandescent lamp 60 to pass from the cavity 48 located at an interior of the at least substantially hollow member 44 to an exterior of the at least substantially hollow member 44. For example, the at least substantially hollow member 44 may include at least one light hole 66 formed in a sidewall of the at least substantially hollow member 44. Thus, at least some light emitted by the incandescent lamp 60 may be visible at the exterior of the at least substantially hollow member 44 as light passes through the light holes 66.

The scent warmer 42 may include a power cord 68 physically secured by, and in electrical communication with, the power cord connector 22 of the base structure 10. The power cord 68 may be physically secured within the recess 26 of the power cord connector 22 due to frictional interference between their abutting surfaces. The power cord 68 may include electrical contacts (not shown) that are in electrical communication with the prongs 28 (see FIGS. 2 through 4) of the power cord connector 22. By way of example, the power cord 68 may include a standard electrical coupler-and-inlet configuration in some embodiments. Standards for coupler-and-inlet power cords 68 may be obtained, for example, from the International Electrotechnical Commission (IEC). Coupler-and-inlet power cords 68 may specifically conform to IEC Standard 60320-1, which sets forth specifications for two-pole couplers for the connection of power supply cords to electrical appliances. Generally, coupler-and-inlet power cords 68 comprise a coupler, typically located on the power cord 68 supplying electrical power to an appliance that interfaces with a complementary inlet, typically located on the appliance. As a specific, non-limiting example, the power cord 68 may comprise a standard C7 coupler.

The power cord 68 may also include a plug 70 configured to engage and electrically communicate with an electrical power outlet. By providing the scent warmer 42 with a power cord 68 and complementary power cord connector 22, a user may more easily assemble the scent warmer 42, exchange the power cord 68 with another power cord to replace a broken or damaged cord, or exchange the power cord 68 to enable the scent warmer 42 to be used in another geographic area where a different configuration for the power plug may be in use, for example. In embodiments where each of the electrical connections is formed using strips 30, 34, 36, 38, and 40 of electrically conductive material, the power cord connector 22 may enable the base structure 10 to be completely free of relatively flexible wires disposed in the interior thereof because the only wires used in connection therewith may be located in the power cord 68, which is located at an exterior of the base structure 10.

When assembling the scent warmer 42, the electrical connector 62 of the incandescent lamp 60 may be engaged with the electrical connector 18 of the support structure 12. The at least substantially hollow member 44 may be disposed over the incandescent lamp 60 and the support structure 12. The lower opening 50 of the at least substantially hollow member 44 may be aligned with the incandescent lamp 60. The incandescent lamp 60 may be at least partially received into the cavity 48 defined by the at least substantially hollow member 44 as the at least substantially hollow member 44 is lowered onto the support structure 12. The at least substantially hollow member 44 may rest on a supporting portion, such as, for example, the retaining portions 16 or other upper surfaces, of the support structure 12. The power cord 68 may be engaged with the power cord connector 22 of the support structure 12. Thus, the scent warmer 42 may be assembled.

Figure 7A:
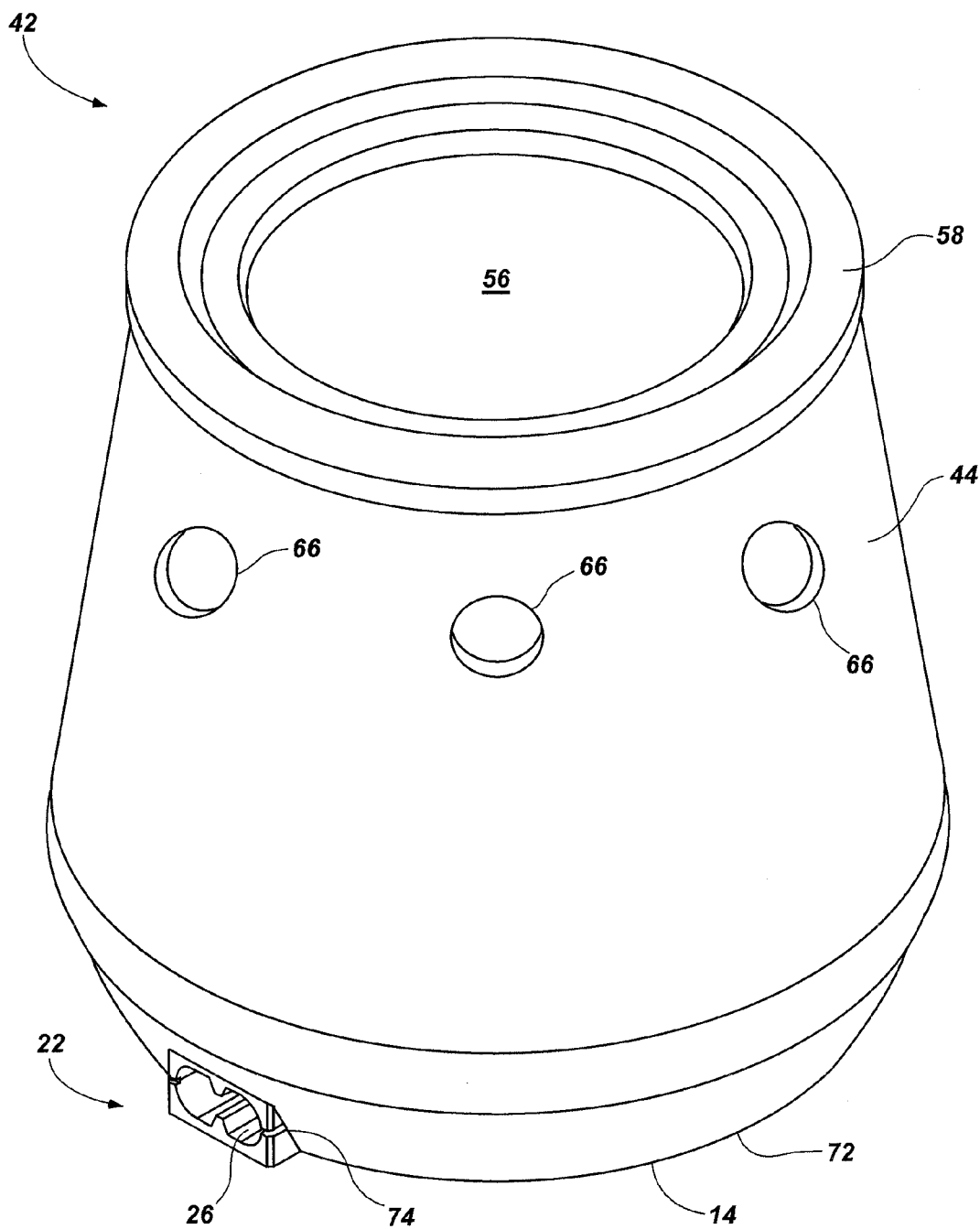
FIG. 7A illustrates a perspective view of the scent warmer of FIG. 5.
Figure 7B:
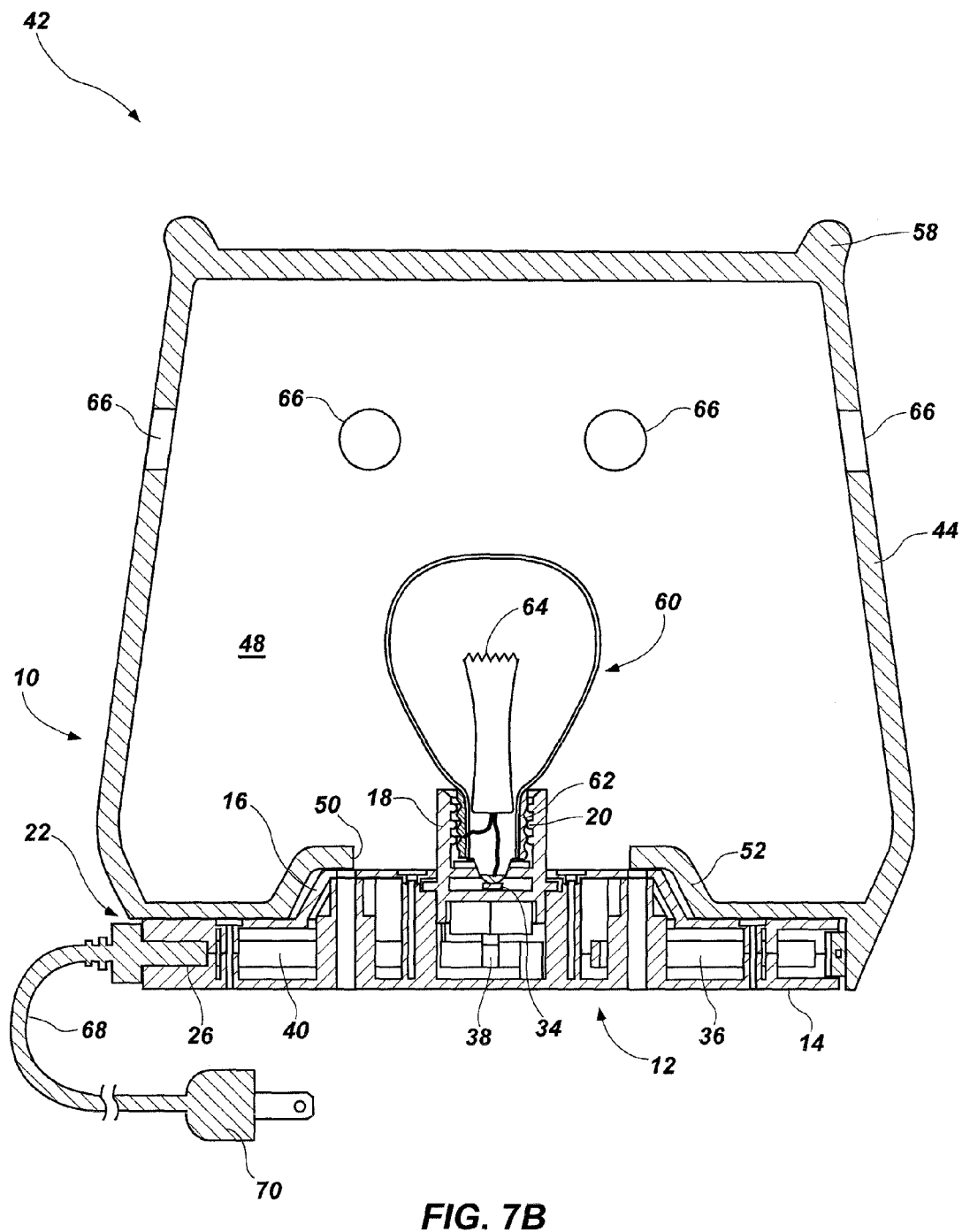
FIG. 7B is a cross-sectional view of the scent warmer of FIG. 7A.

Referring to FIG. 7A, a perspective view of the scent warmer 42 of FIG. 5 is shown. Referring to FIG. 7B, a cross-sectional view of the scent warmer 42 of FIG. 7A is shown. As shown in FIGS. 7A and 7B, the receptacle 46 (see FIG. 6) may be removed from the scent warmer 42, revealing the upper surface 56 of the at least substantially hollow member 44. When the at least substantially hollow member 44 is disposed on the support member 12, the at least substantially hollow member 44 may extend downwardly such that a lower surface 72 of the at least substantially hollow member 44 is at least substantially flush with the lower surface 14 of the support structure 12. Thus, the at least substantially hollow member 44 may conceal all of the support structure 12 except for the power cord connector 22 and the optional switch 24, which may be accessible through notches 74 in the at least substantially hollow member 44.

Figure 8:
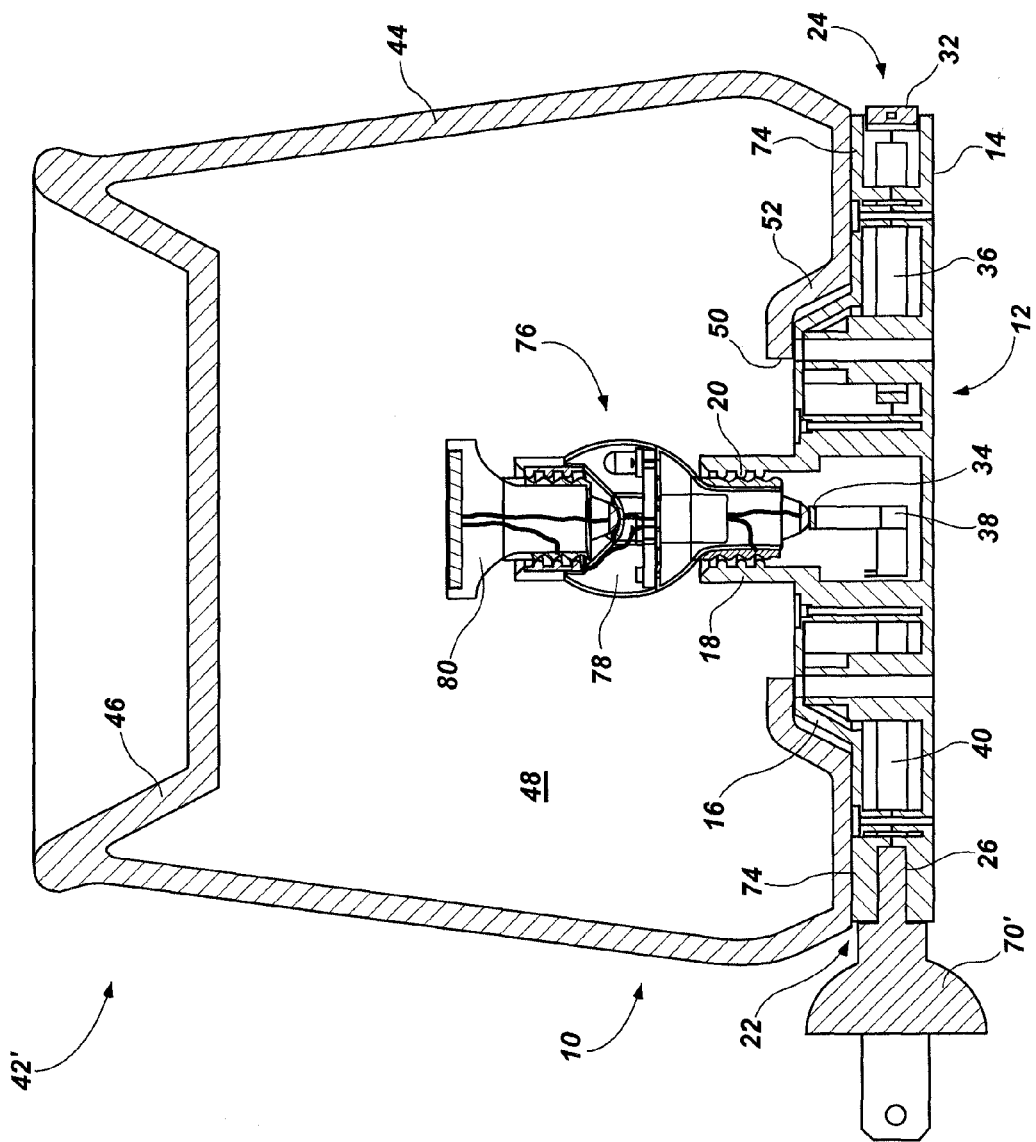
FIG. 8 is a cross-sectional view another embodiment of a scent warmer.

Referring to FIG. 8, a cross-sectional view another embodiment of a scent warmer 42' is shown. As shown in FIG. 8, the lighting, heating, or lighting and heating module connected to the electrical connector 18 of the base structure 10 may comprise an assembly 76 of a lighting module 78 and a heating module 80, as described more fully with reference to FIGS. 9 through 17. Rather than an extended power cord 68, as shown in FIG. 6, the scent warmer 42' may include a plug 70', which may be rigidly connected to the base structure 10 using the power cord connector 22. Thus, the scent warmer 42' may be configured to be supported by the plug 70' when the plug 70' is inserted into an electrical outlet, rather than resting on the lower surface 14 of the base member 10. The receptacle 46 may not be removable from the at least substantially hollow member 44. For example, the receptacle 46 and the at least substantially hollow member 44 may comprise a single, integral structure.

Rather than, or in addition to, forming light holes 66 (see FIGS. 6, 7A and 7B) in the sidewalls of the at least substantially hollow member 44, the material of the at least substantially hollow member 44 may be translucent. Accordingly, at least some light emitted by the lighting or lighting and heating module at least partially disposed in the cavity 48 defined by the at least substantially hollow member 44 may pass through the material of the at least substantially hollow member 44. The at least substantially hollow member 44 may be transparent in some embodiments. In other embodiments, the at least substantially hollow member 44 may diffuse light emitted by the lighting or lighting and heating module such that only some of the light passes through the material of the at least substantially hollow member 44. The translucent material of the at least substantially hollow member 44 may be colored in some embodiments. For example, the translucent material of the at least substantially hollow member 44 may absorb at least some wavelengths of visible light while permitting other wavelengths of light to pass through, imparting a hue to the light that passes through the at least substantially hollow member 44. In some embodiments, the translucent material of the at least substantially hollow member 44 may be patterned with opaque designs or with two or more colors of translucent material.

Figure 9:
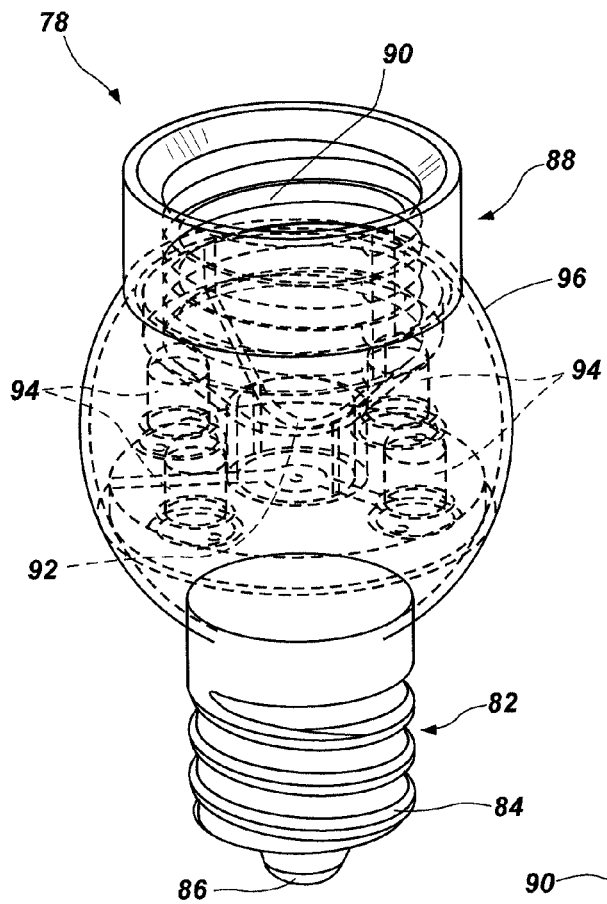
FIG. 9 is a perspective view of a lighting module that may be used with a scent warmer.
Figure 10:
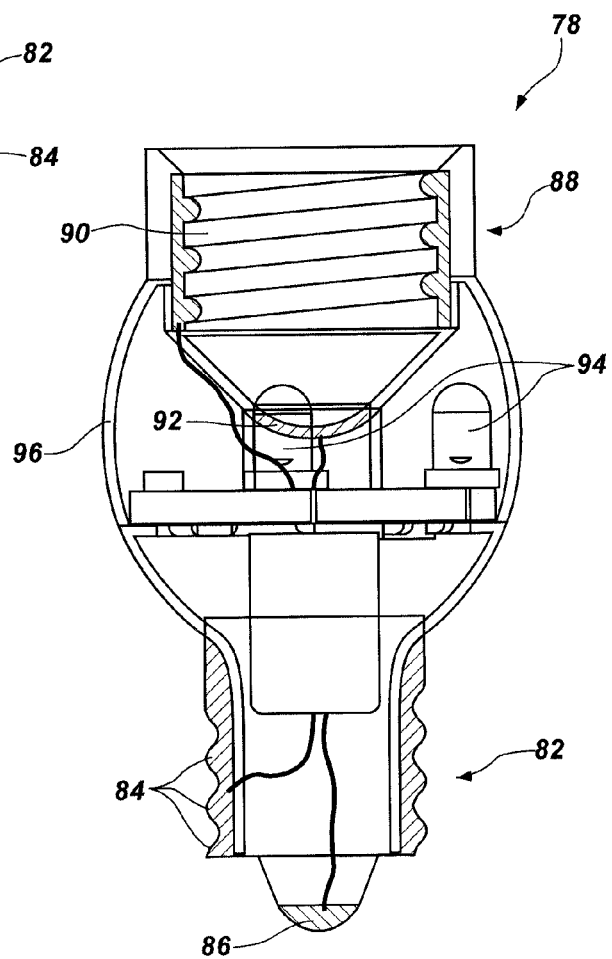
FIG. 10 depicts a cross-sectional view of the lighting module of FIG. 9.

Referring to FIGS. 9 and 10, a perspective view and a cross-sectional view of a lighting module 78 that may be used with a scent warmer are shown, respectively. The lighting module 78 comprises a lower electrical connector 82. The lower electrical connector 82 may be disposed at a lower portion of the lighting module 78. Thus, the lighting module 78 may be configured for physical and electrical engagement with an electrical connector 18 of a base structure 10 (see FIG. 8). The lower electrical connector 82 may comprise at least one helically extending protrusion 84 configured to threadedly engage and electrically communicate with a helically extending recess 90 (see FIG. 8) and at least one contact 86 configured to electrically communicate with a contact of the electrical connector 18 (see FIG. 8) to form a closed electrical path. At least a portion of the lower electrical connector 82 may comprise an electrically conductive material and may be configured to receive electrical power from an electrical power source.

The lower electrical connector 82 may comprise a male Edison screw fitting. As a specific, non-limiting example, the lower electrical connector 82 may comprise a standard E11 Edison screw fitting, which may correspond to a standard candelabra size Edison screw fitting as used in Europe. As another specific, non-limiting example, the lower electrical connector 82 may comprise a standard E27, also known in the art as a standard "ES," Edison screw fitting, which may correspond to a medium, or standard size, light bulb Edison screw fitting as used in Europe. The lower electrical connector 82 may comprise the same size Edison screw fitting as the electrical connector 18 of the base structure 10 (see FIG. 8).

The lighting module 78 may further comprise an upper electrical connector 88. The upper electrical connector 88 may be disposed at an upper portion of the lighting module 78. Thus, the lighting module 78 may be configured to receive an electrical connector from above the lighting module 78. The upper electrical connector 88 may comprise at least one helically extending recess 90 configured to threadedly engage and electrically communicate with a male threaded electrical connector and at least one contact 92 configured to communicate with a contact of the male threaded electrical connector to form a closed electrical path. At least a portion of the upper electrical connector 88 may comprise an electrically conductive material and may be in electrical communication with the lower electrical connector 82. For example, a pass-through electrical connection may provide electrical communication between the lower electrical connector 82 and the upper electrical connector 88. Thus, a single power source may provide electrical power to both the lower electrical connector 82 and the upper electrical connector 88.

The upper electrical connector 88 may comprise a female Edison screw fitting. As a specific, non-limiting example, the upper electrical connector 88 may comprise a standard E11 Edison screw fitting, which may correspond to a standard candelabra size Edison screw fitting as used in Europe. As another specific, non-limiting example, the upper electrical connector 88 may comprise a standard E27, also known in the art as a standard "ES," Edison screw fitting, which may correspond to a medium, or standard size, light bulb Edison screw fitting as used in Europe. The upper electrical connector 88 may comprise the same size Edison screw fitting as the lower electrical connector 82 in some embodiments. In other embodiments, the upper electrical connector 88 may comprise a different size Edison screw fitting from the lower electrical connector 82.

The lighting module 78 may comprise at least one electrical light source 94 interposed between the lower electrical connector 82 and the upper electrical connector 88. Thus, the lower electrical connector 82 may be disposed on a first, lower side of the electrical light source 94, and the upper electrical connector 88 may be disposed on another, upper side of the electrical light source 94 opposing the first, lower side on which the lower electrical connector 82 is disposed. As shown in FIGS. 9 and 10, a plurality of electrical light sources 94 may be disposed in an array between the lower electrical connector 82 and the upper electrical connector 88. For example, four electrical light sources 94 may be distributed in a substantially uniformly spaced array around a periphery of the lighting module 78. The electrical light sources 94 may be in electrical communication with the lower electrical connector 82. For example, a pass-through electrical connection may provide electrical communication between the lower electrical connector 82 and the electrical light sources 94. Thus, a single power source may provide electrical power to the lower electrical connector 82, the upper electrical connector 88, and the electrical light sources 94.

The lighting module 78 may include a cover member 96. The cover member 96 may be used to structurally connect the lower electrical connector 82 to the upper electrical connector 88. The cover member 96 may comprise an at least substantially hollow member that defines an inner cavity in which the electrical light sources 94 may be disposed. At least a portion of the cover member 96 may comprise a translucent material. By way of example, the cover member 96 may comprise a translucent polymer material. Accordingly, at least some light emitted by the electrical light sources 94 may pass through the cover member 96. The cover member 96 may be transparent in some embodiments. In other embodiments, the cover member 96 may diffuse light emitted by the electrical light sources 94 such that only some of the light passes through the cover member 96. The cover member 96 may also include holes formed therethrough, which may enable light emitted by the electrical light sources 94 to pass from the internal cavity of the cover member 96 to an exterior of the cover member 96. The translucent material of the cover member 96 may be colored in some embodiments. For example, the translucent material of the cover member 96 may absorb at least some wavelengths of visible light while permitting other wavelengths of light to pass through, thereby imparting a desired hue to the light that passes through the cover member 96. In other embodiments, the translucent material of the cover member 96 may be patterned with opaque designs, or with two or more colors of translucent material.

Figure 11:
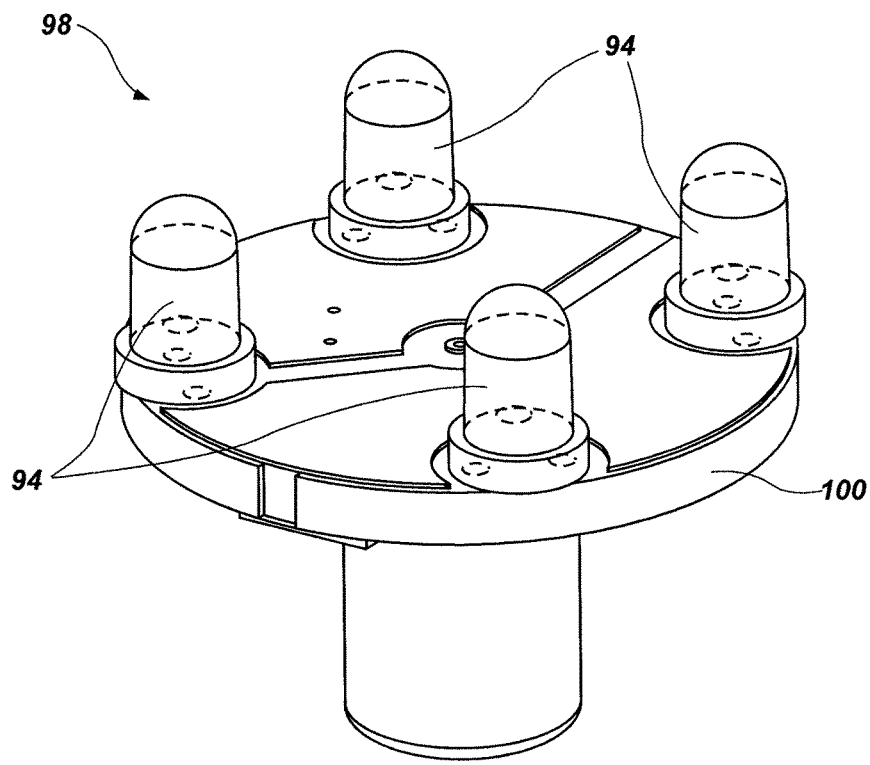
FIG. 11 illustrates a perspective view of an assembly of electrical light sources that may be used with the lighting module of FIG. 9.

Referring to FIG. 11, a perspective view of an assembly 98 of electrical light sources 94 that may be used with the lighting module 78 of FIG. 1 is shown. The electrical light sources 94 may be provided in an array on a carrier substrate 100, such as, for example, a printed circuit board, which may structurally connect and support the electrical light sources 94. The electrical light sources 94 may be filamentless. For example, the electrical light sources 94 may comprise light-emitting diodes (LEDs) or compact fluorescent lamps (CFLs). In embodiments where the electrical light sources 94 comprise LEDs, the electrical light sources 94 may comprise single-colored LEDs or LEDs of a design capable of changing color. For example, the electrical light sources 94 may comprise an array of LEDs capable of emitting red, green, and blue light, alone or in combination with one another, sometime referred to as "RGB LEDs." Thus, the electrical light sources 94, the cover member 96 (see FIGS. 9 and 10), or both may act to impart a hue to light emitted by the lighting module 78 (see FIGS. 9 and 10).

Figure 12:
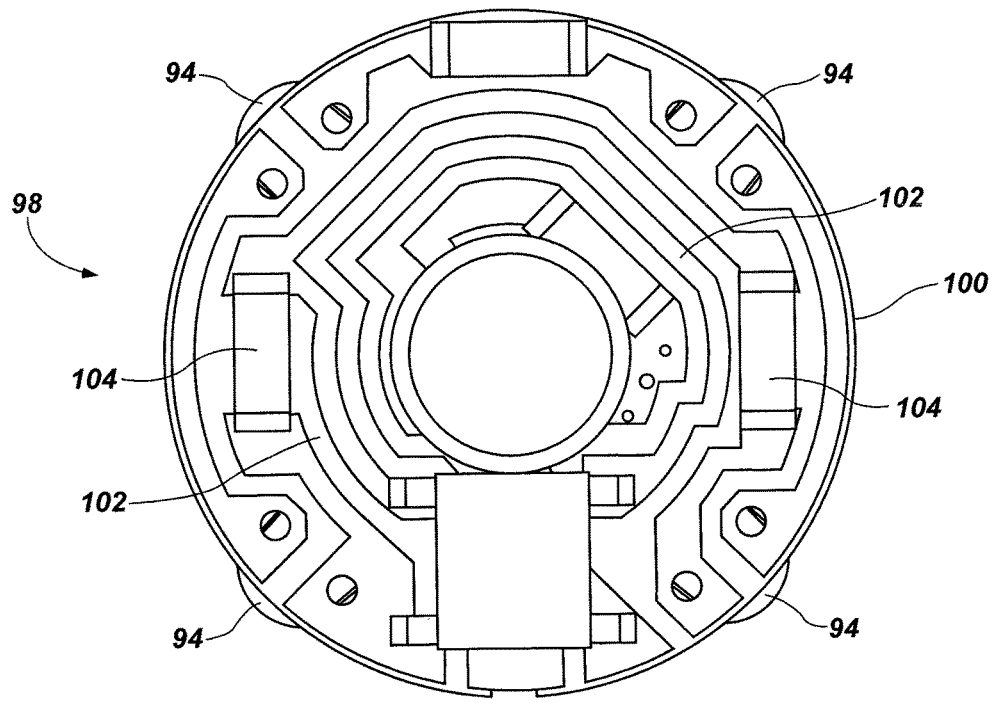
FIG. 12 is a plan view from below the assembly of electrical light sources of FIG. 11 depicting circuitry that may be used with the assembly of electrical light sources.

Referring to FIG. 12, a plan view from below the assembly 98 of electrical light sources 94 of FIG. 3 depicts circuitry that may be used with the assembly of electrical light sources. The carrier substrate 100 may comprise an electrically conductive material configured to electrically communicate with the lower electrical connector 82 of a lighting module 78 (see FIGS. 1 and 2) and with the electrical light sources 94. For example, the carrier substrate 100 may include metal traces 102 disposed on a surface thereof in electrical communication with the electrical light sources 94 and configured to electrically communicate with the lower electrical connector 82 of a lighting module 78 (see FIGS. 1 and 2). The carrier substrate 100 may also comprise circuitry 104 configured to control at least one of intensity, flickering, and coloring of visible light emitted by the electrical light sources 94. For example, the carrier substrate 100 may comprise circuitry 104 in electrical communication with the electrical light sources 94 via the traces 102 that may be configured to change at least one of intensity, flickering, and coloring of electrical light sources 94 comprising LEDs in response to a user input. In addition or in the alternative, the circuitry 104 may be configured to convert Alternating Current (AC) electrical power to Direct Current (DC) electrical power, known in the art as an AC rectifier circuit. As a specific, non-limiting example, the circuitry 104 may enable a user to selectively change the electrical light sources 94 from emitting substantially constant white light of a first intensity to emitting flickering yellow light of a second, dimmer intensity. In another non-limiting example, circuitry 104 may comprise one or more power conversion modules to reduce household power (e.g., current) input to electrical light sources 94, or to upper electrical connector 88, or both, as desired.

Figure 13:
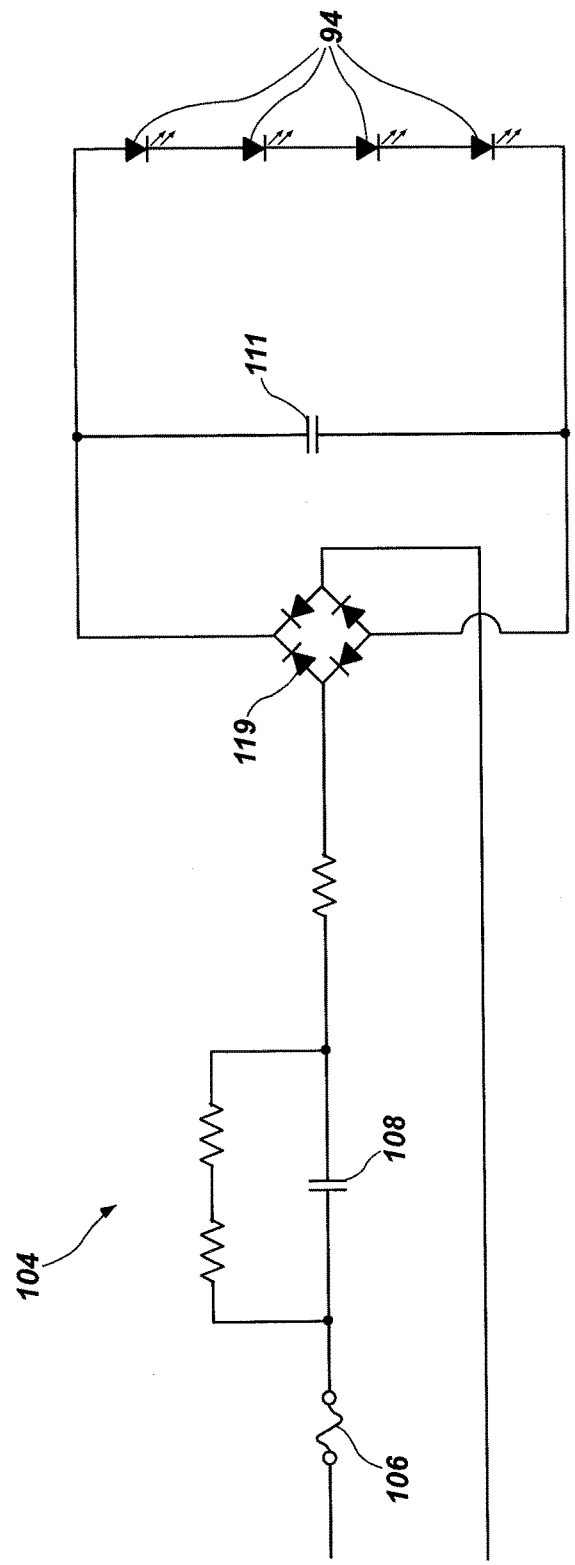
FIG. 13 is a circuit diagram of a circuit that may be used with the assembly of electrical light sources of FIG. 11.

Referring to FIG. 13, one embodiments of a circuit diagram of a circuit 104 that may be used with the assembly 98 of electrical light sources 94 of FIG. 11 is shown. As depicted, the circuit 104 may comprise a fuse 106 configured to prevent excessive and potentially damaging current levels from flowing through the circuit 104, for example, to electrical light sources 94. For example, the fuse 106 may comprise a 200 mA fuse. The circuit 104 may also comprise a parallel resistor-capacitor (RC) circuit 108. For example, the parallel RC circuit 108 may comprise resistors having a total resistance of 660 k$\Omega$ in parallel with capacitors having a total capacitance of 0.33 µF. The capacitor in the parallel RC circuit 108 may diminish the amplitude and fluctuation of current (e.g., fluctuation of direct current, fluctuation of alternating current, or simply high amplitude portions of alternating current) flowing through the circuit 104, while the resistors may enable the capacitor to discharge after the circuit 104 has been disconnected from an electrical power source. Additional resistors, capacitors, and other electrical components may be used, as needed or desired. The circuit 104 may include a diode bridge 119 configured to provide the same polarity output regardless of the polarity of input to the circuit 104. By including a reservoir capacitor 111 in parallel with the electrical light sources 94, the circuit 104 may act as an AC rectifier due to the smoothing provided by the reservoir capacitor 111 in connection with the diode bridge 119.

Figure 14:
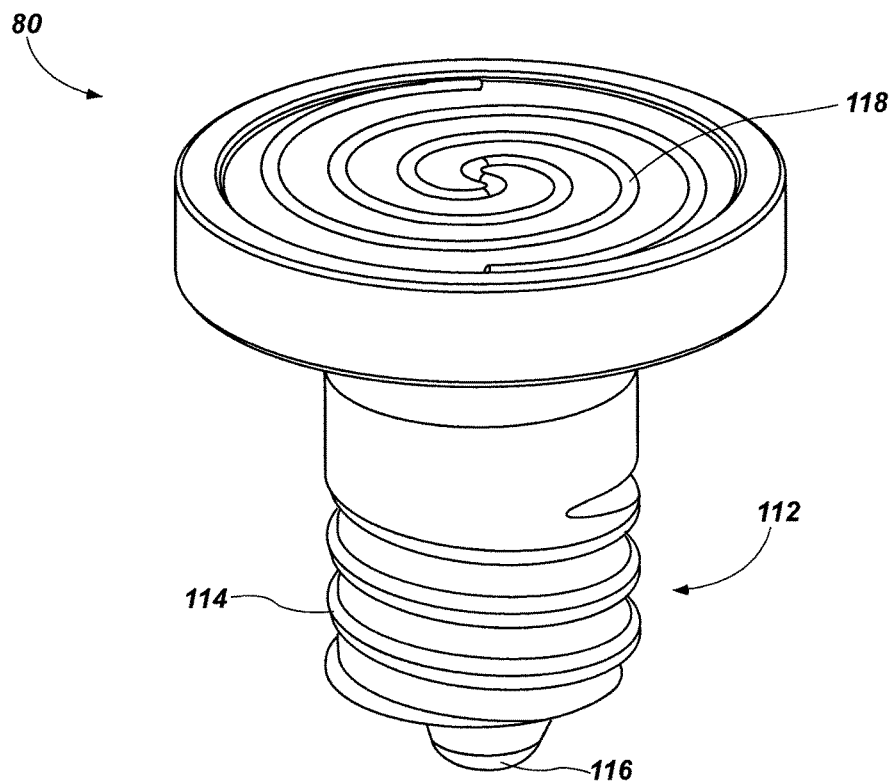
FIG. 14 illustrates a perspective view of a heating module that may be used with a scent warmer.
Figure 15:
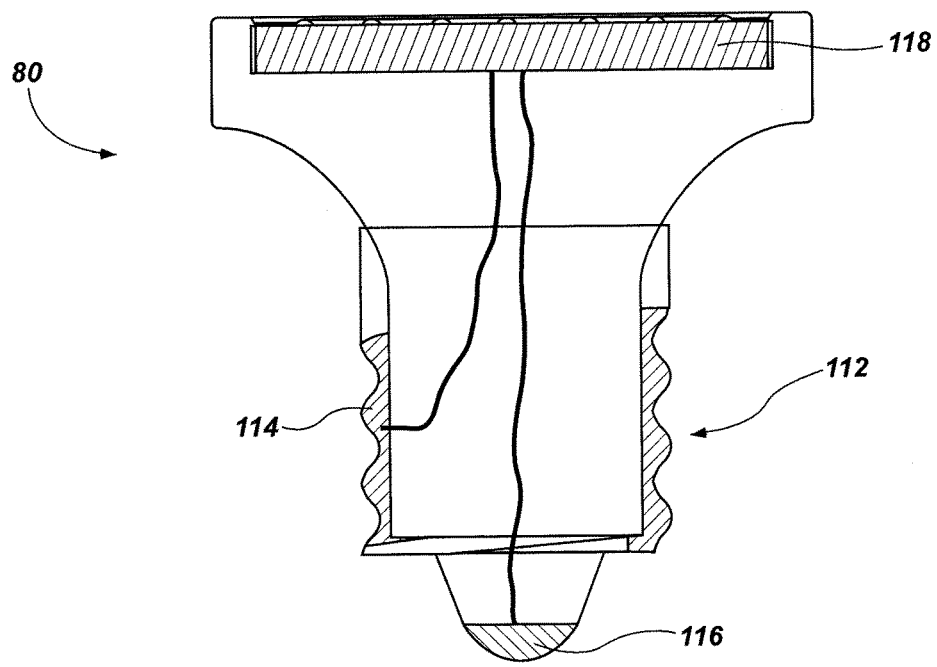
FIG. 15 is a cross-sectional view of the heating module shown in FIG. 14.

Referring to FIGS. 14 and 15, a perspective view and a cross-sectional view of a heating module 80 that may be used with a scent warmer are shown, respectively. The heating module 80 may comprise a lower electrical connector 112 configured for physical and electrical engagement with an upper electrical connector 88 of a lighting module 78 (see FIGS. 9 and 10). The lower electrical connector 112 may be disposed at a lower portion of the heating module 80. The lower electrical connector 112 may comprise at least one helically extending protrusion 114 configured to threadedly engage and electrically communicate with the helically extending recess 90 of an upper electrical connector 88 of a lighting module 78 and at least one contact 116 configured to electrically communicate with the contact 92 of the upper electrical connector 88 of the lighting module 78 (see FIGS. 1 and 2) to form a closed electrical path. At least a portion of the lower electrical connector 112 may comprise an electrically conductive material and may be configured to receive electrical power from the upper electrical connector 88 of the lighting module 78 (see FIGS. 1 and 2).

The lower electrical connector 112 may comprise a male Edison screw fitting. As a specific, non-limiting example, the lower electrical connector 112 may comprise a standard E11 Edison screw fitting, which may correspond to a standard candelabra size Edison screw fitting as used in Europe. As another specific, non-limiting example, the lower electrical connector 112 may comprise a standard E27, also known in the art as a standard "ES," Edison screw fitting, which may correspond to a medium, or standard, size light bulb Edison screw fitting as used in Europe. The lower electrical connector 112 may comprise the same size Edison screw fitting as the upper electrical connector 88 of a lighting module 78 (see FIGS. 1 and 2). Thus, the heating module 80 may be configured for mechanical and electrical connection to a lighting module 78 (see FIGS. 1 and 2).

The heating module 80 may comprise a heating element 118. The heating element 118 may be disposed at an upper portion of the heating module 80 above the lower electrical connector 112. Thus, the heating element 118 may be located at an end of the heating module 80 opposing the lower electrical connector 112. The heating element 118 may be electrically connected to the lower electrical connector 112 and configured to receive electrical power therefrom. The heating element 118 may comprise, for example, a resistive element, such as a filament-type or ceramic element, an infrared element, a Peltier-type element, a thermocouple element, or an inductive heating element, which would heat a receptacle having a ferrous lining or insert.

The heating element 118 may be configured to heat to a temperature suitable for warming a scented material. The heating element 118 may also be configured to only heat to a temperature sufficiently low that the scented material being warmed does not ignite and that the heating module 80 and any other devices near the heating element 118 retain structural integrity (i.e., do not experience catastrophic failure due to temperature-induced weakening of the materials from which they are formed). For example, the heating element 118 may be configured to heat to a temperature of between about 45° C. and 70° C. As a continuing example, the heating element 118 may be configured to heat to a temperature of between about 50° C. and about 60° C. In one non-limiting example, heating module 80 may incorporate a power conversion module to reduce household power (e.g., current) input. Another approach is incorporation of a thermocouple in the circuit to remove power from heating element 118 when the temperature becomes undesirably high.

Referring to FIGS. 16 and 17, a perspective view and a cross-sectional view of an assembly 76 of the lighting module 78 of FIGS. 9 and 10 with the heating module 80 of FIGS. 14 and 15 are shown, respectively. The lower electrical connector 112 of the heating module 80 may be threadedly engaged with the upper electrical connector 88 of the lighting module 78. Thus, the assembly 76 may be configured to emit both light and heat using the lighting module 78 and the heating module 80, respectively.

When assembling the assembly 76, the heating module 80 may be positioned over the lighting module 78, and the lower electrical connector 112 of the heating module 80 may be aligned with the upper electrical connector 88 of the lighting module 78. The heating module 80 may be simultaneously lowered and rotated with respect to the lighting module 78. Thus, the helically extending protrusion 114 of the lower electrical connector 112 of the heating module 80 may engage with the helically extending recess 90 of the upper electrical connector 88 of the lighting module 78. As the lower electrical connector 112 of the heating module 80 proceeds downwardly into the upper electrical connector 88 of the lighting module 78, the contact 116 of the lower electrical connector 112 of the heating module 80 may abut the contact 92 of the upper electrical connector 88 of the lighting module 78 to form a closed electrical path. For example, the electrical connection thus formed may comprise a pass-through electrical connection. Thus, electrical power provided to the lower electrical connector 82 of the lighting module 78 may be transmitted to both the lighting module 78 and the heating module 80, and the components thereof. For example, a single electrical power source may transmit electrical power to the lower electrical connector 82 of the lighting module 78, the electrical light sources 94 of the lighting module 78, the upper electrical connector 88 of the lighting module 78, the lower electrical connector 112 of the heating module 80, and the heating element 118 of the heating module 80.

While certain embodiments have been described herein, those of ordinary skill in the art will recognize and appreciate that the disclosure is not so limited. Rather, many additions, deletions, and modifications to the embodiments described herein may be made without departing from the scope of the invention as hereinafter claimed, including legal equivalents. In addition, features from one embodiment may be combined with features of another embodiment while still being encompassed within the scope of the invention as contemplated by the inventor.

CONCLUSION

In some embodiments, base structures for use with a scent warmer comprise a support structure configured to receive thereon an at least substantially hollow member defining an internal cavity. An electrical connector extends from the support structure. A power cord connector extending from the support structure is electrically connected to the electrical connector using a rigid electrical connection and configured to physically secure and electrically communicate with a power cord.

In other embodiments, scent warmers configured to heat a scented material and emit light comprise a base structure and at least one of a lighting module, a heating module, and a lighting and heating module. The base structure comprises a support structure. An at least substantially hollow member defining an internal cavity is disposed on the support structure. A receptacle for supporting a scented material is disposed over the at least substantially hollow member. An electrical connector extends from the support structure toward the cavity defined by the at least substantially hollow member. A power cord connector extending from the support structure is electrically connected to the electrical connector using a rigid electrical connection and configured to physically secure and electrically communicate with a power cord. The at least one of a lighting module, a heating module, and a lighting and heating module is disposed at least partially within the cavity defined by the at least substantially hollow member of the base structure and comprises an electrical connector engaged and in electrical communication with the electrical connector of the base structure. At least one of an electrical light source and an electrical heat source is located above and in electrical communication with the electrical connector.

In additional embodiments, methods of making a base structure for use with a scent warmer comprise configuring a support structure to receive thereon an at least substantially hollow member defining an internal cavity. An electrical connector that extends from the support structure is formed. A power cord connector configured to physically secure and electrically communicate with a power cord is electrically connected with the electrical connector using a rigid electrical connection.

In further embodiments, methods of assembling a scent warmer comprise engaging an electrical connector of at least one of a lighting module, a heating module, and a lighting and heating module with an electrical connector of a support structure. An at least substantially hollow member defining a cavity is disposed over the at least one of the lighting module, the heating module, and the lighting and heating module and rested on a supporting portion of the support structure. A power cord is engaged with a power cord connector of the support structure.

What is claimed is:

1. A scent warmer, comprising:
a hollow member having at least one inner surface defining an internal cavity therein;
a receptacle disposed at a first longitudinal end of the hollow member for holding scented material therein; and
a support structure configured to support at least one lighting module within the internal cavity of the hollow member, the support structure comprising:
a first rigid electrical connector extending continuously from a first side of the support structure to a second, opposite side of the support structure;
a second rigid electrical connector extending from the first side of the support structure to at least one of a lighting module, a heating module, and a lighting and heating module;
an intermediate rigid electrical connector extending from the at least one of the lighting module, the heating module, and the lighting and heating module to the second, opposite side of the support structure; and
a planar lower surface and at least one retaining portion extending from the planar lower surface, the at least one retaining portion comprising a frustoconical protrusion,
wherein the support structure is a discrete and separable member from the hollow member, the hollow member is configured to rest upon the support structure, and the hollow member is configured to conceal at least a portion of the support structure when the hollow member is placed over the support structure on a flat surface.

2. The scent warmer of claim 1, wherein a lower surface of the hollow member is configured to be flush with the planar lower surface of the support structure when the hollow member is placed over the support structure on a flat surface.

3. The scent warmer of claim 1, wherein the intermediate rigid electrical connector is coupled to the lighting and heating module and the lighting and heating module comprises an incandescent lamp.

4. The scent warmer of claim 1, wherein the intermediate rigid electrical connector extends longitudinally upward from the support structure, and further comprising:
a power cord connector extending from the first side of the support structure electrically connected to the intermediate rigid electrical connector by the second rigid electrical connector; and
a power cord configured to physically and electrically connect to and disconnect from the power cord connector.

5. The scent warmer of claim 4, wherein the hollow member includes a notch defined in a second longitudinal end thereof, the notch configured to permit the power cord of the scent warmer to extend therethrough.

6. The scent warmer of claim 1, wherein at least one portion of the hollow member comprises a translucent material.

7. The scent warmer of claim 1, wherein the receptacle is separable from the hollow member.

8. The scent warmer of claim 1, wherein the hollow member comprises an angled surface and the support structure comprises a correspondingly beveled surface, the angled surface configured to rest upon the correspondingly beveled surface.

9. A scent warmer configured to heat a scented material and emit light, comprising:
a support structure, the support structure comprising a first rigid electrical connector extending continuously from a first side of the support structure to a second, opposite side of the support structure, a second rigid electrical connector extending from the first side of the support structure to at least one of a lighting module, a heating module, and a lighting and heating module, an intermediate rigid electrical connector extending from the at least one of the lighting module, the heating module, and the lighting and heating module to the second, opposite side of the support structure, a planar lower surface, and at least one retaining portion extending from the planar lower surface, the at least one retaining portion comprising a frustoconical protrusion;
a hollow member defining an internal cavity and disposed over the support structure, the support structure being a discrete and separable member from the hollow member, the hollow member being configured to rest upon the support structure, wherein a lower surface of the hollow member is configured to be flush with the planar lower surface of the support structure when the hollow member is placed over the support structure on a flat surface; and a receptacle disposed at a first longitudinal end of the hollow member for supporting the scented material.

10. The scent warmer of claim 9, wherein the hollow member is configured to conceal at least a portion of the support structure when the hollow member is placed over the support structure on the flat surface.

11. The scent warmer of claim 9, wherein the intermediate rigid electrical connector extends longitudinally upward from the support structure, and further comprising:

a power cord connector extending from the first side of the support structure electrically connected to the intermediate rigid electrical connector by the second rigid electrical connector; and a power cord configured to physically and electrically connect to and disconnect from the power cord connector.

12. The scent warmer of claim 9, wherein the support structure comprises a polymeric material and the hollow member and receptacle comprise a ceramic material.

13. The scent warmer of claim 9, wherein the at least one of the lighting module, the heating module, and the lighting and heating module comprises at least one lighting module supported by the support structure.

14. The scent warmer of claim 9, wherein the at least one of a lighting module, a heating module, and a lighting and heating module comprises the lighting and heating module and comprises an incandescent lamp.

15. The scent warmer of claim 9, wherein the hollow member comprises an angled surface and the support structure comprises a correspondingly beveled surface, the angled surface configured to rest upon the correspondingly beveled surface.

16. A method of using a scent warmer, comprising:

placing a support structure having at least one lighting module supported thereon on a flat surface, the support structure comprising a first rigid electrical connector extending continuously from a first side of the support structure to a second, opposite side of the support structure, a second rigid electrical connector extending from the first side of the support structure to the at least one lighting module, an intermediate rigid electrical connector extending from the at least one lighting module to the second, opposite side of the support structure, a planar lower surface, and at least one retaining portion extending from the planar lower surface, the at least one retaining portion comprising a frustoconical protrusion;

placing a hollow member comprising an internal cavity over the support structure such that the at least one lighting module is received into the internal cavity of the hollow member and such that the hollow member conceals at least a portion of the support structure;

providing a scented material in a receptacle disposed on a first longitudinal end of the hollow member; and heating the scented material using the at least one lighting module.

17. The method of claim 16, wherein placing the hollow member defining an internal cavity over the support structure further comprises placing the hollow member over the support structure such that a lower surface of the hollow member is flush with the planar lower surface of the support structure.

18. The method of claim 16, wherein placing the hollow member defining an internal cavity over the support structure further comprises placing a lower surface of the hollow member in contact with the flat surface.

19. The method of claim 16, wherein placing the hollow member over the support structure comprises placing an angled surface of the hollow member over a correspondingly beveled surface of the support structure.

* * * * *

UNITED STATES PATENT AND TRADEMARK OFFICE
CERTIFICATE OF CORRECTION

PATENT NO. : 9,775,925 B2
APPLICATION NO. : 14/686689
DATED : October 3, 2017
INVENTOR(S) : Brandon Juarez It is certified that error appears in the above-identified patent and that said Letters Patent is hereby corrected as shown below:

In the Specification
Column 3, Line 53, change "(i transmitting light" to --(i.e., transmitting light--

Signed and Sealed this
Thirtieth Day of January, 2018

Joseph Matal
*Performing the Functions and Duties of the*
*Under Secretary of Commerce for Intellectual Property and*
*Director of the United States Patent and Trademark Office*